United States Patent
Cope et al.

(10) Patent No.: US 6,168,209 B1
(45) Date of Patent: Jan. 2, 2001

(54) KEYED CAP FOR GAS OUTLET VALVE

(75) Inventors: Robert L. Cope, Lawrenceville; Roger A. Davis, Suwanee; David D. Seem, Alpharetta; James D. Gomez, Norcross; Phillip B. Plyler, Atlanta; Max E. Raby, Norcross; Andrew J. Cisternino, Atlanta; Robert P. Dutlinger, Alpharetta; Eric J. Kaplan, Atlanta; James E. Bullington, Buford, all of GA (US)

(73) Assignee: Hill-Rom Medaes, Inc., Norcross, GA (US)

(*) Notice: Under 35 U.S.C. 154(b), the term of this patent shall be extended for 0 days.

(21) Appl. No.: 09/183,516

(22) Filed: Oct. 30, 1998

Related U.S. Application Data

(60) Provisional application No. 60/064,321, filed on Oct. 30, 1997.

(51) Int. Cl.⁷ .................................................. F16L 21/04
(52) U.S. Cl. ........................................ 285/330; 285/914
(58) Field of Search ................................. 285/914, 330; 137/331, 382

(56) References Cited

U.S. PATENT DOCUMENTS

| | | | |
|---|---|---|---|
| 2,282,552 | * 5/1942 | Banowetz | 285/914 |
| 2,394,363 | * 2/1946 | Bynoe | 285/914 |
| 3,004,777 | 10/1961 | Buonaccorsi . | |
| 3,170,667 | * 2/1965 | Szohatzky | 285/914 |
| 3,194,588 | * 7/1965 | Buckey et al. | 285/914 |
| 4,150,673 | * 4/1979 | Watt | 285/914 |
| 4,253,685 | * 3/1981 | Camp | 285/41 |
| 4,619,640 | 10/1986 | Potolsky et al. . | |
| 4,665,960 | * 5/1987 | Brzezicki et al. | 285/914 |
| 4,696,326 | 9/1987 | Sturgis . | |
| 4,718,699 | 1/1988 | Kulish et al. . | |
| 4,790,567 | * 12/1988 | Kawano et al. | 285/24 |
| 5,197,511 | 3/1993 | Kohn et al. . | |
| 5,725,511 | 3/1998 | Urrutia . | |

FOREIGN PATENT DOCUMENTS

| | | | |
|---|---|---|---|
| 1187435 | * 2/1965 | (DE) | 285/914 |
| 2141249 | * 3/1972 | (DE) | 285/914 |
| 372373 | * 6/1990 | (EP) | 285/914 |
| 2406776 | 5/1979 | (FR) . | |
| 2625545 | 7/1989 | (FR) . | |
| 2642139 | 7/1990 | (FR) . | |
| 275992 | * 11/1989 | (JP) | 285/914 |

* cited by examiner

Primary Examiner—Eric K. Nicholson
(74) Attorney, Agent, or Firm—Barnes & Thornburg

(57) ABSTRACT

A gas valve apparatus is configured to receive a gas specific adapter. The apparatus includes a gas valve body having a first end configured to be coupled to a gas connection and a second end. A keyed body is configured to receive the second end of the gas valve body. The keyed body has a first keying mechanism. The apparatus also includes a cap coupled to the keyed body. The cap includes a keyed front face having a gas outlet configured to receive the gas specific adapter. The cap also includes a second keying mechanism configured to mate with the first keying mechanism on the keyed body to permit the cap to be coupled to the keyed body.

19 Claims, 9 Drawing Sheets

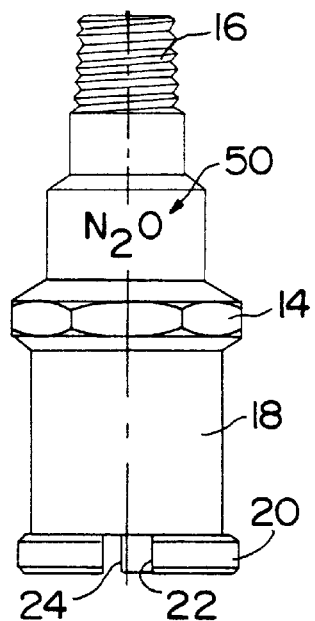
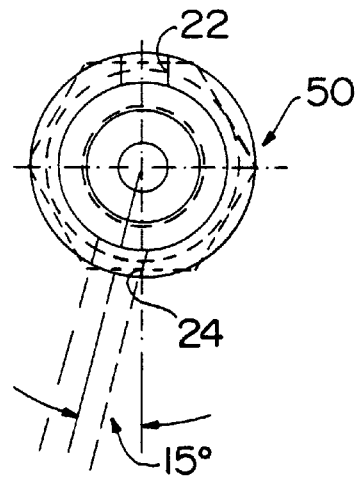
FIG. 9  FIG. 10
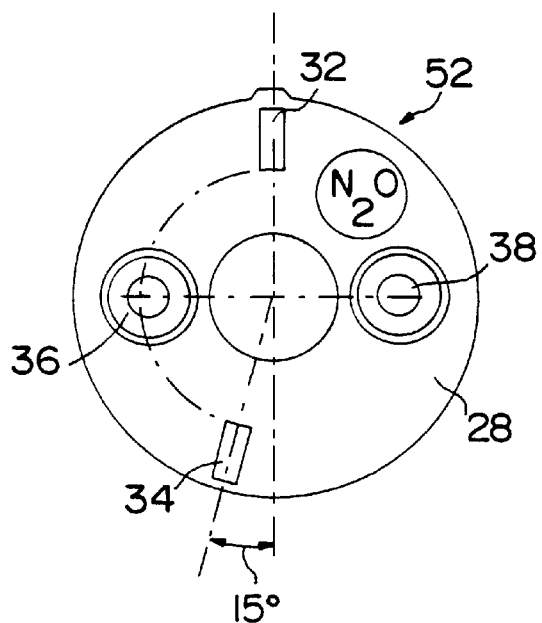
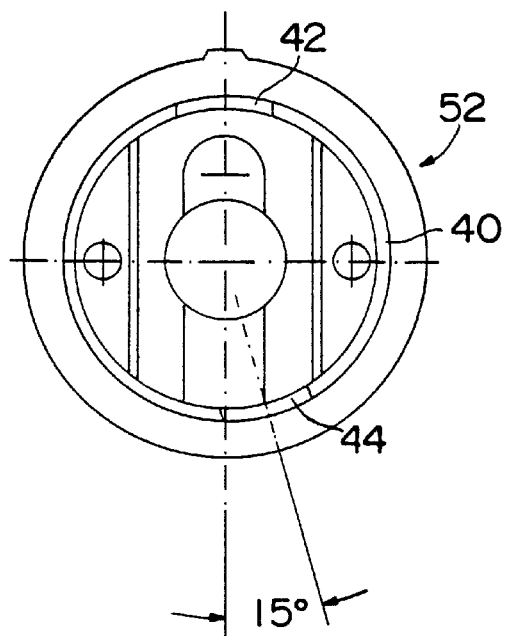
FIG. 11  FIG. 12

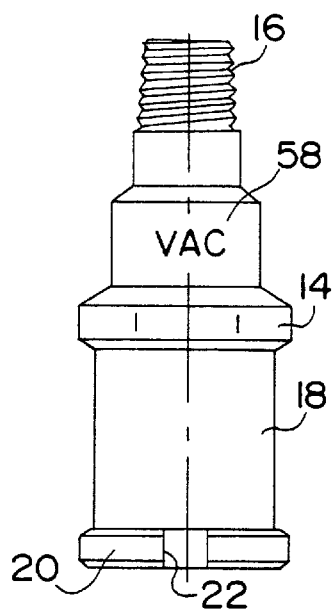
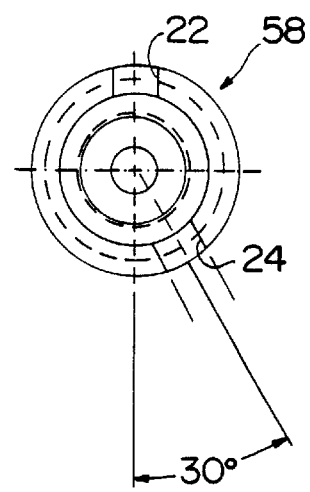
FIG.17
FIG.18
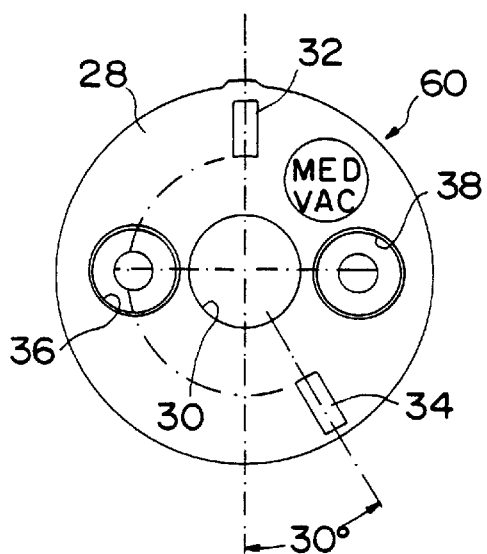
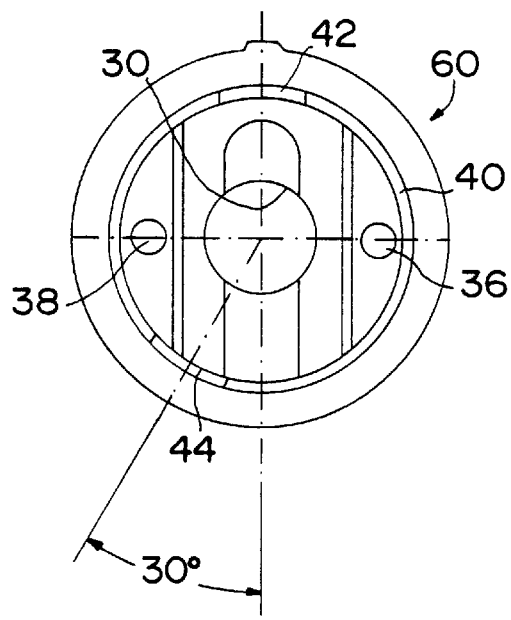
FIG.19
FIG.20

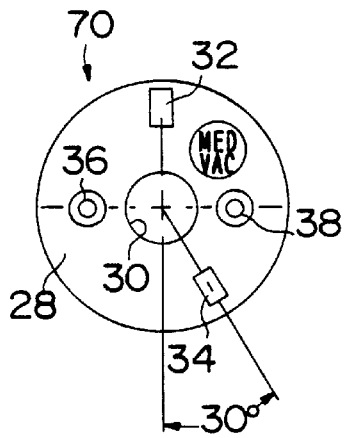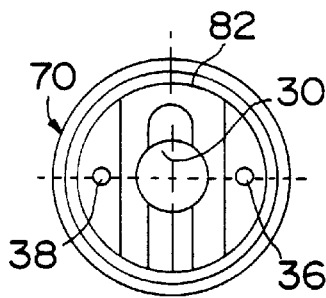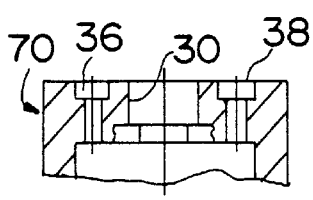
FIG.21  FIG.23  FIG.22
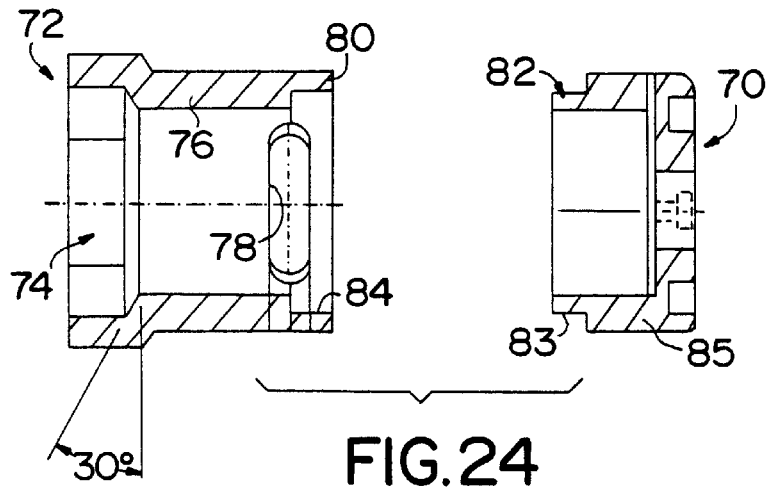
FIG.24
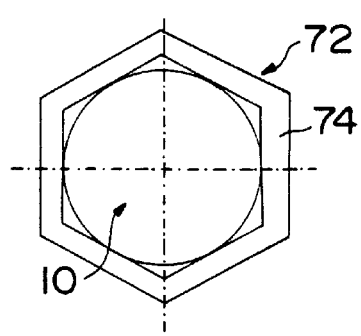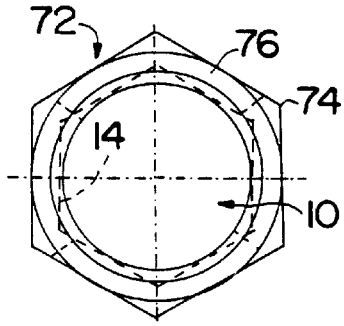
FIG.25  FIG.26

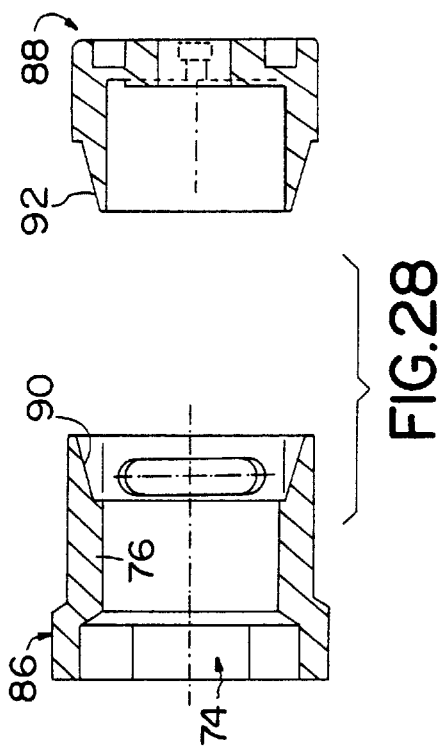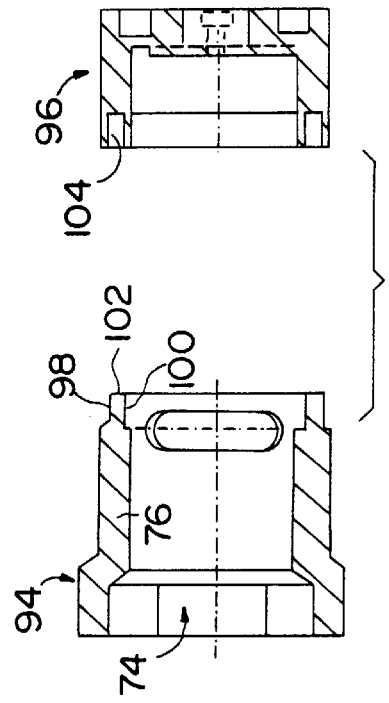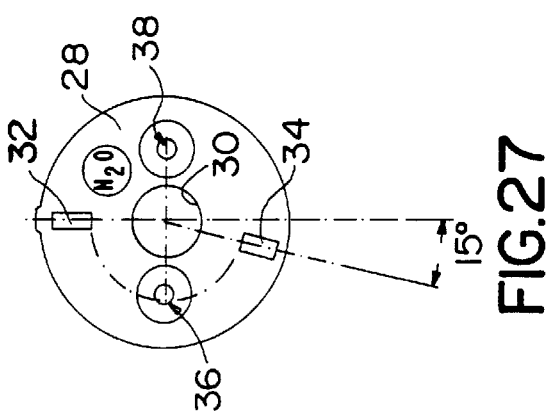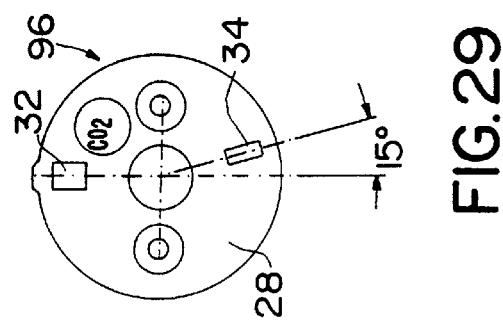

KEYED CAP FOR GAS OUTLET VALVE

This application claims the benefit of U.S. provisional application Serial No. 60/064,321 filed Oct. 30, 1997.

BACKGROUND AND SUMMARY OF THE INVENTION

The present invention relates to an improved cap apparatus for a gas outlet valve. More particularly, the present invention relates to a cap and body portion which are keyed to provide a plurality of different specific gas outlets to ensure that a proper cap is installed on a particular gas specific gas outlet valve.

It is known to provide gas outlet valves coupled to movable gas blocks within head walls of hospital rooms or other locations to supply gases to a room. More specifically, gas valves may be connected to a hose in an operating room ("O/R") column, or to a hose barb and hose suspended from a ceiling as a pendant. Seven gas outlets are typically made available including oxygen, air, nitrous oxide, nitrogen, carbon dioxide, helium, and vacuum. Typically, gases are supplied to the hospital room through a gas manifold. Gas outlet blocks are connected to the manifold by hoses. Gas outlet valves have gas specific threads for coupling the valves to the outlet blocks. The conventional gas outlet valves include a valve body having a check valve, an internal spring, and poppet valve. A cap is coupled to the valve body. The cap has a clock face which is keyed to be gas specific for adapters that are connected to the clock face of the cap.

After a predetermined amount of use, the gas outlet valves must be serviced. Particularly, the valves are removed to replace O-ring seals within the valve. In order to gain access to the inside of the valve, the caps are removed. A problem associated with conventional gas outlet valves and caps is that the caps may be inadvertently installed onto the wrong gas outlet valve after servicing.

The present invention provides a gas specific, keyed cap which is only able to be coupled to a matching gas outlet valve. This keyed cap of the present invention reduces the likelihood that the wrong gas cap will be installed on a specific gas outlet valve.

According to one aspect of the present invention, a gas valve apparatus is configured to receive a gas specific adapter. The apparatus includes a gas valve body having a first end configured to be coupled to a gas connection and a second end. The second end has an outer lip formed to include first and second spaced apart slots.

The apparatus also includes a cap coupled to the gas valve body. The cap includes a keyed front face having a gas outlet configured to receive the gas specific adapter. The cap also includes a flange formed to include first and second spaced apart tabs configured to enter the first and second spaced apart slots, respectively, to permit the cap to be coupled to the gas valve body.

In an illustrated embodiment, the front face of the cap includes a pair of keys spaced apart by a predetermined angle. The pair of keys on the cap are configured to mate with a pair of keys on the gas specific adapter. The first and second spaced apart slots formed in the ring of the gas valve body and the first and second spaced apart tabs formed on the cap also are spaced apart at the predetermined angle.

Also in an illustrated embodiment, the gas valve body is configured to be coupled to one of a gas block, a hose in an O/R column, and a hose barb and hose suspended from a ceiling as a pendant. The gas valve body and the gas specific adapter are each configured to supply one of oxygen, air, nitrous oxide, nitrogen, carbon dioxide, helium and vacuum.

In the illustrated embodiments, the first and second spaced apart slots and the first and second tabs are each spaced apart by an angle of 180°, 165°, 150°, or 135° depending upon the type of gas. It is understood that other angles may be used in accordance with the present invention.

According to another aspect of the present invention, a gas valve apparatus is configured to receive a gas specific adapter. The apparatus includes a gas valve body having a first end configured to be coupled to a gas connection and a second end, and a keyed body configured to receive the second end of the gas valve body. The keyed body has a first keying mechanism. The apparatus also includes a cap coupled to the keyed body. The cap includes a keyed front face having a gas outlet configured to receive the gas specific adapter. The cap also includes a second keying mechanism configured to mate with the first keying mechanism on the keyed body to permit the cap to be coupled to the keyed body.

In one illustrated embodiment, the first keying mechanism includes an annular groove having a predetermined diameter formed in the keyed body, and the second keying mechanism includes an annular flange formed on the cap. The annular flange has substantially the same predetermined diameter as the annular groove to permit the flange to mate with the groove formed in the keyed body.

In another the illustrated embodiment, the keyed body includes a cylindrical portion having inner and outer side walls. The annular groove is formed by a notch formed adjacent the inner side wall. The annular flange of the cap includes an inner side wall and an outer side wall. The flange is formed to include a notched portion adjacent the outer side wall to permit the flange to be inserted into the annular groove. In yet another the illustrated embodiment, the annular groove and the annular flange are each tapered surfaces.

In still another the illustrated embodiment, the first keying mechanism includes an annular ring formed on the keyed body, and the second keying mechanism includes an annular groove formed in the cap. The annular ring has a predetermined diameter, and the annular groove has substantially the same predetermined diameter as the annular ring to permit the annular ring to mate with the annular groove when the cap is installed on the keyed body.

In an illustrated embodiment, the gas valve body includes a hex nut located between the first and second ends, and the keyed body is formed to include a hex portion configured to engage the hex nut on the valve body to prevent rotation of the keyed body relative to the gas valve body. The gas valve body is secured to the keyed body by an adhesive. Illustratively, the keyed body and the cap are made from a material having the same color.

Additional objects, features, and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying drawings in which:

FIGS. 9 and 10 illustrate details of a nitrous oxide gas valve body;

FIGS. 11 and 12 illustrate a keyed cap configured to be coupled to the nitrous oxide gas valve of FIGS. 9 and 10;

FIGS. 17 and 18 illustrate a vacuum valve body;

FIGS. 19 and 20 illustrate a keyed cap configured to be coupled to the vacuum valve body of FIGS. 17 and 18;

FIGS. 21–23 illustrate another embodiment of a keyed cap of the present invention;

FIG. 24 illustrates another keying apparatus of the present invention including a keyed body configured to be located over an end of the gas valve body and a keyed cap configured to be coupled to the keyed body;

FIGS. 24, 25, and 26 illustrate a hex portion of the keyed body configured to receive a hex nut on the gas valve body;

FIGS. 27 and 28 illustrate another embodiment of the present invention in which the keyed body and the keyed cap include mating tapered sections;

FIGS. 29 and 30 illustrate another embodiment of the present invention in which the keyed body is formed to include an annular flange configured to be located within an annular groove formed in the keyed cap;

DETAILED DESCRIPTION OF THE DRAWINGS

Figure 1:
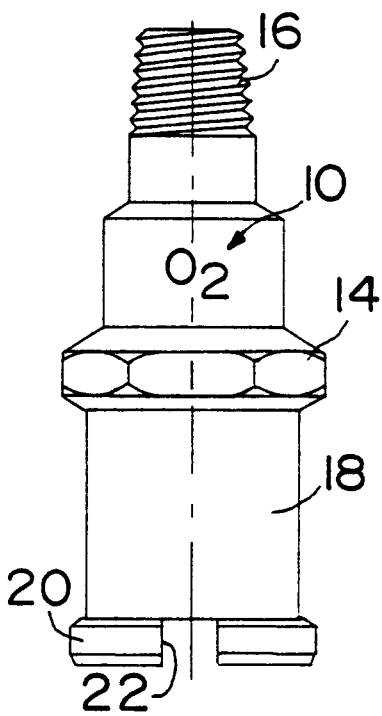
FIG. 1 is a top view of a gas valve body.
Figure 2:
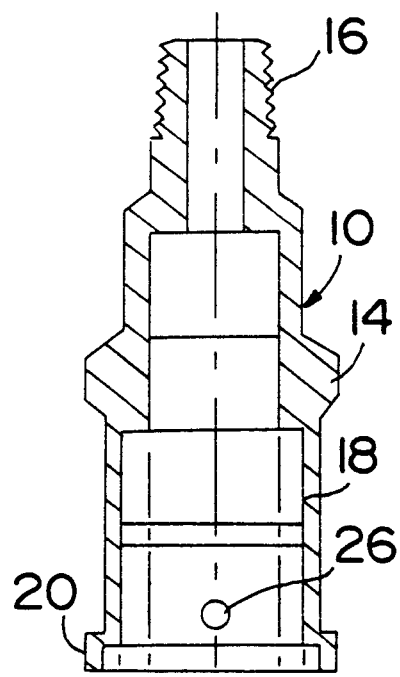
FIG. 2 is a sectional view taken through the gas valve body of FIG. 1.
Figure 3:
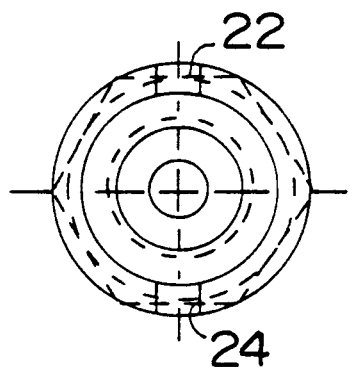
FIGS. 3 and 4 illustrate additional details of the gas valve body.
Figure 4:
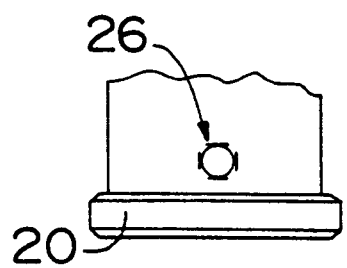
Figure 5:
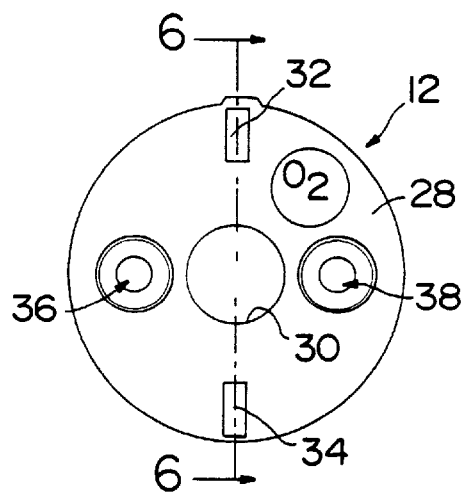
FIG. 5 is a front side elevational view of a keyed cap configured to be installed on the gas outlet body of FIG. 1.

FIGS. 1–8 of the drawings illustrate a first embodiment of the present invention including an improved gas outlet valve body 10 and cap 12. The valve body 10 includes a hex nut 14 and threads 16 for coupling the valve body 10 to a gas block, or any other suitable gas connection such as a hose in an O/R column, or a hose barb and hose suspended from the ceiling as a pendant. The threads 16 are ¼ inch NPT. The valve body 10 includes a cylindrical portion 18 and an elevated lip or ring 20 formed integrally with cylindrical body 18 as best illustrated in FIG. 2. The ring 20 is formed to include a pair of angularly spaced apart slots 22 and 24 to provide gas specific slots configured to receive the cap 12. The valve body 10 includes threaded apertures 26 at diametrically opposed positions for receiving set screws (not shown) which extend through the valve body 10 to hold internal components of the valve in place.

A problem associated with conventional caps is that the caps are interchangeable on to various types of valve bodies. In other words, when the cap is removed for servicing of components of the valve, the cap may inadvertently be placed on the wrong type of gas valve body. Conventional valve bodies do not have the keying feature of the present invention. The present invention is designed to provide a keyed cap for both connection to an adapter coupled to the cap 12 and also for connection between the cap 12 and the valve body 10.

Figure 6:
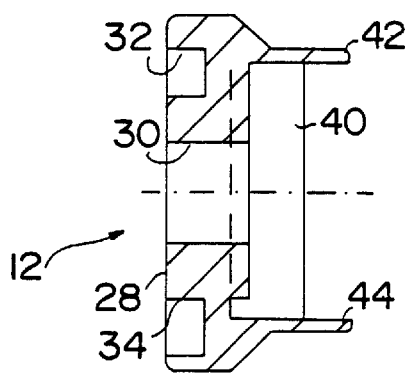
FIG. 6 is a sectional view taken along lines 6—6 illustrating further details of the keyed cap.
Figure 7:
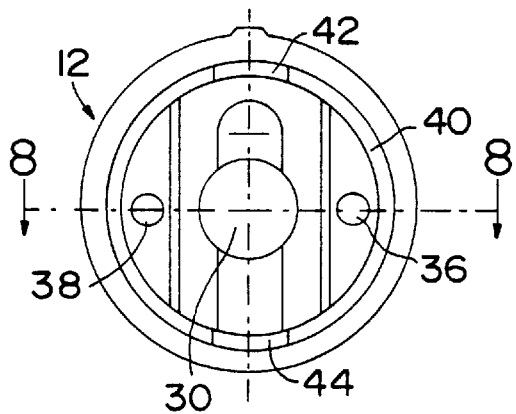
FIG. 7 is a rear elevational view of the cap of FIG. 5.
Figure 8:
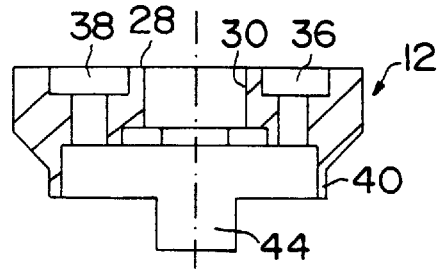
FIG. 8 is a sectional view taken along lines 8—8 of FIG. 7.
Figure 13:
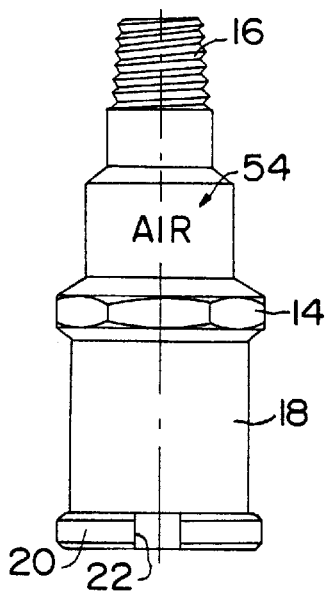
FIGS. 13 and 14 illustrate a gas valve body for supplying air.

An oxygen valve body 10 is illustrated in FIGS. 1–4. The oxygen cap 12 is illustrated in FIGS. 5–8. The cap 12 includes front clock face 28 which is formed to include a gas outlet opening 30 and a pair of keyed slots 32 and 34. Keyed slots 32 and 34 are configured to receive tabs on an adapter coupled to the cap 12 so that the adapter is gas specific. A pair of screw holes 36 and 38 permit screws to pass through cap 12 and engage components of the valve. As illustrated in FIG. 6, cap 12 includes a flange 40 and a pair of tabs 42 and 44 which are sized to fit within slots 22 and 24, respectively, formed in ring 20 of valve body 10. The tabs 44 of cap 12 are formed at the same angular locations as slots 22 and 24, respectively, so that the cap 12 is specifically keyed for the oxygen valve body 10 illustrated in FIGS. 1–4. Further details of the cap 12 are illustrated in FIGS. 7 and 8.

Additional embodiments of the present invention are illustrated in FIGS. 9–20. Those numbers referenced by numbers same as FIGS. 1–8 perform the same or similar function.

FIGS. 9–12 illustrate a nitrous oxide valve body 50 and cap 52. As best illustrated in FIG. 10, the bottom slot 24 is located at a 15° angle to the left of center. The second key slot 34 of cap 52 is also located at a 15° angle to the left of center. The bottom tab 44 of cap 52 is aligned at the same 15° angle to match the slot 24 of the keyed valve body 50. Therefore, the valve body 50 is keyed only to receive the nitrous oxide cap having properly aligned tabs 42 and 44 for entering slots 22 and 24, respectively.

Figure 14:
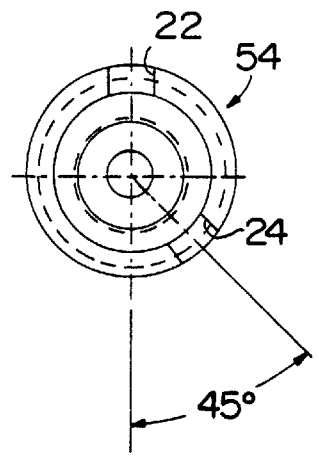
Figure 15:
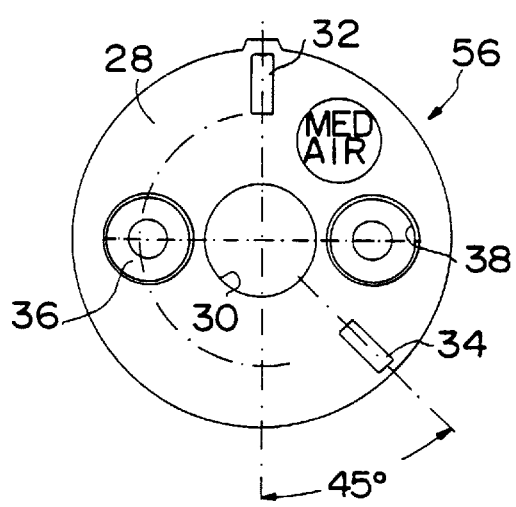
FIGS. 15 and 16 illustrate a keyed cap configured to be coupled to the air gas valve body of FIGS. 13 and 14.
Figure 16:
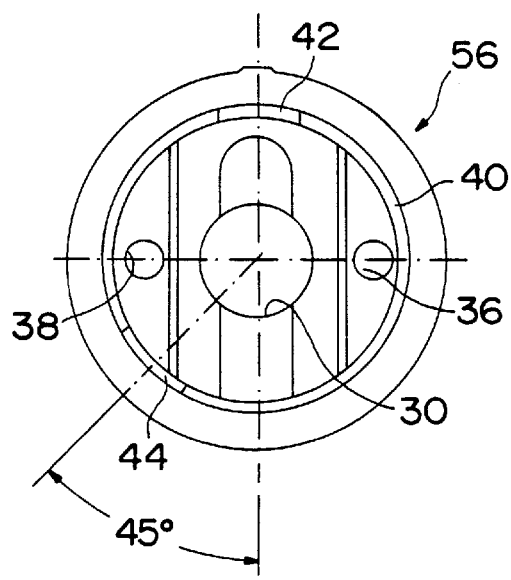

FIGS. 13–16 illustrate a valve body 54 and cap 56 which are illustratively designed for use with air. As illustrated in FIG. 14, the bottom slot 24 in the ring 20 of valve body 54 is aligned at a 45° angle to the right of center. The bottom keying slot 34 is also aligned at a 45° angle to provide a keyed clock face 16 for a medical air adapter. In addition, the bottom tab 44 is aligned at a 45° angle to correspond to the location of slot 24 of the air valve body 54. Therefore, the cap 56 can only be coupled to the air valve body 54.

FIGS. 17–20 illustrate a valve body 58 for a medical vacuum and a specific valve cap 60 for the medical vacuum valve body 58. The bottom slot 24 of the valve body 58 is aligned at a 30° angle to the right of center as illustrated in FIG. 18. The bottom slot 34 of cap 60 is also aligned at a 30° angle to provide a gas specific keying for the adaptor configured to be coupled to the medical vacuum cap 60. In addition, the bottom tab 44 of cap 60 is aligned at a 30° angle to correspond to the location of the bottom slot 24 of valve body 58. Therefore, cap 60 can only be coupled to the specific vacuum valve body 58.

It is understood that other gas valve bodies and caps may be made by adjusting the alignment of the slots 22 and 24 and tabs 42 and 44, respectively. By changing the angles between the slots 22 and 24 and tabs 42 and 44, only a specific cap can be coupled to a specific valve body. This prevents the wrong type of cap from being installed on a particular gas valve body.

Other embodiments of the present invention are illustrated in FIGS. 21–36. Again, these embodiments are designed to provide gas-specific keying for caps so that only a specific cap can be mounted to a specific valve body. FIG. 21 illustrates a sample cap 70 for medical gas. Those numbers referenced on cap 70 which are identical to the numbers of prior figures perform the same or similar function. FIG. 22 is a sectional view taken through the cap 70 illustrating screw holes 36 and 38. FIG. 23 is a rear view of cap 70.

FIG. 24 illustrates a keyed body 72 configured to fit over conventional valve body to provide keying for the cap 70. The conventional valve body is similar to the valve body illustrated above except that the valve body does not include the outer lip 20. The conventional valve bodies do include the cylindrical body portion 18 and hex portion 14.

The keyed body 72 includes a hex portion 74 and a cylindrical body portion 76. Keyed body 72 slides over an end of the conventional valve body until the hex portion 74 engages the hex portion of valve body as illustrated in FIGS. 25 and 26. This engagement prevents rotation of the keyed body 72 relative to the conventional valve body. The keying body 72 is also glued to the valve body. Body 72 is formed to include a pair of slots 78 on opposite sides of the body 72 to permit insertion and withdrawal of set screws (not shown) through an aperture in the side portion of the valve body.

The keyed body 72 includes an annular ring 80 having dimensions as illustrated in FIG. 24. A notched portion 84 is formed in inner wall 76 to define the dimensions of the annular ring 80. The cap 70 includes an inner projection 82 formed by notched portion 83 of flange 85. Projection 82 is sized to slide past sidewall 84 of annular portion 80 of valve body 72. Illustratively, this keying arrangement for medical vacuum cap 70 prevents the vacuum cap 70 from being installed on another type of keyed gas body described below.

Illustratively, the cap 70 and valve body 72 are formed from the same color material to provide a visual indication of the proper cap for connecting to the outlet body 72. Illustratively, the color for body 72 and cap 70 is white.

Another embodiment of the keyed body 86 and keyed cap 88 is illustrated in FIGS. 27 and 28. In this embodiment, the cap 88 is illustratively used for nitrous oxide. The keyed body 86 fits over conventional gas valve body around cylindrical portion 18 and over hex portion 14 as discussed above. Keyed body portion 86 includes an inwardly tapered female portion 90. Keyed cap 88 includes an inwardly tapered male portion 92 configured to slide within tapered portion 90 of the keyed valve body 86. Illustratively, the keyed valve body 86 and cap 88 are formed from a blue material.

FIGS. 29 and 30 illustrate another embodiment of a keyed valve body 94 and keyed cap 96 for carbon dioxide. In the FIG. 30 embodiment, the cylindrical portion 76 is notched on both the inner and outer sides at locations 98 and 100, respectively, to form an annular ring 102. The cap 96 is formed to include an annular groove 104 aligned with the annular ring 102 and sized to fit over the annular ring 102. Illustratively, both the keyed body 94 and cap 96 for carbon dioxide are made of a grey material.

Figure 32:
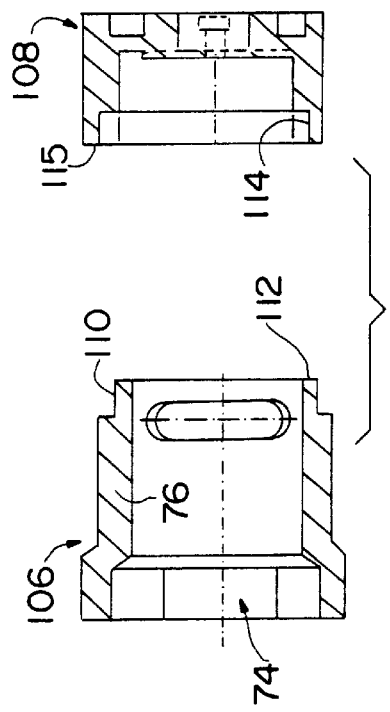
FIGS. 31 and 32 illustrate yet another embodiment of the present invention in which a flange of the keyed cap is configured to be inserted over an annular ring formed on the keyed body.
Figure 31:
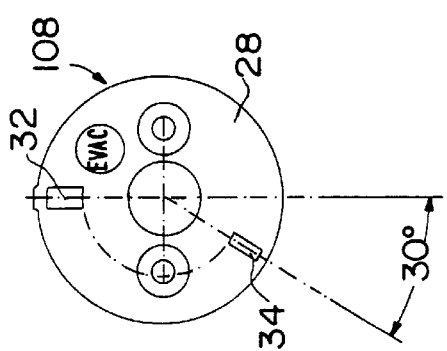

FIGS. 31 and 32 illustrate another keyed body 106 and keyed cap 108 for use with evacuation. In this embodiment, the keyed valve body 106 includes a notched section 110 extending inwardly from an outer surface of cylindrical body 76. This notched section 110 forms an annular ring 112 having an outer diameter as illustrated in FIG. 32. Keyed cap 108 includes a notched section 114 defining an annular ring 115 sized to fit over annular ring 112 of the keyed body 106 to provide a gas specific cap 108 for the keyed valve body 106. Illustratively, keyed valve body 106 and cap 108 are formed from a violet colored material.

Figure 34:
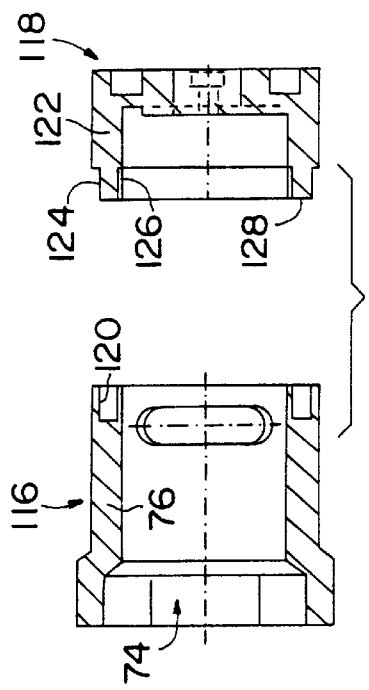
FIGS. 33 and 34 illustrate another embodiment of the present invention in which the keyed body is formed to include an annular groove configured to receive an annular flange formed on the keyed cap.
Figure 33:
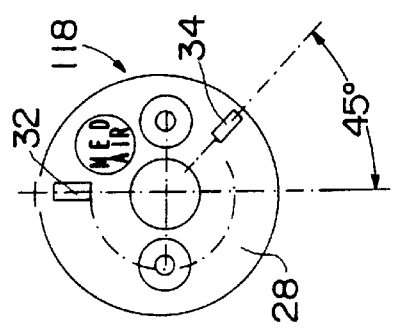

FIGS. 33 and 34 illustrate yet another embodiment of a keyed valve body 116 and keyed cap 118 for use with, for example, medical air. The keyed valve body 116 includes an annular groove 120 formed in cylindrical portion 76. A flange 122 of cap 118 is formed to include a notched portion 124 on an outer side and a notched portion 126 on an inner side of flange 122. This provides an annular ring 128 sized to fit within annular groove 120 formed in keyed valve body 116. This provides a keyed cap 118 which fits only within the specific keyed valve body 116. Illustratively, keyed valve body 116 and cap 118 are formed from a yellow colored material.

Figure 35:
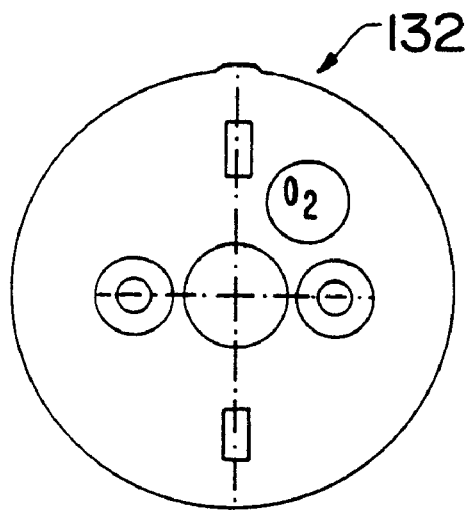
FIGS. 35 and 36 illustrate a further embodiment of the present invention illustrating another annular groove formed in the keyed body configured to mate with an annular flange formed on the keyed cap.
Figure 36:
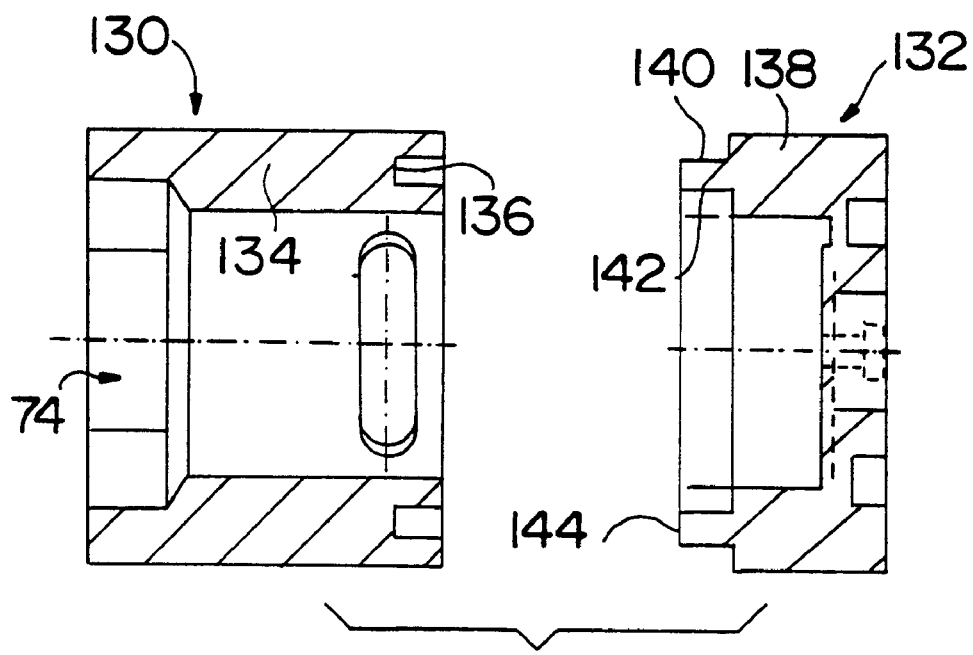

FIGS. 35 and 36 illustrate a further embodiment of a keyed valve body 130 and keyed cap 132 for use with, for example, oxygen. The keyed valve body 130 includes a thicker cylindrical sidewall 134 having an annular groove 136 formed therein. Flange 138 of cap 132 is formed to include notched sections 140 and 142 configured to define annular ring 144. Annular ring 144 is sized to fit within annular groove 136 of keyed valve body 130. Illustratively, both the keyed valve body 130 and keyed cap 132 are formed from a green material.

What is claimed is:

1. A gas valve apparatus configured to receive a gas specific adapter, the apparatus comprising:

a gas valve body having a first end configured to be coupled to a gas connection and a second end, the second end having an outer lip formed to include first and second spaced apart slots; and a cap coupled to the gas valve body, the cap including a keyed front face having a gas outlet configured to receive the gas specific adapter, the cap also including a flange formed to include first and second spaced apart tabs configured to enter the first and second spaced apart slots, respectively, to permit the cap to be coupled to the gas valve body, and a set screw coupled to the gas valve body adjacent the outer lip.

2. The apparatus of claim 1, wherein the front face of the cap includes a pair of keys spaced apart by a predetermined angle, the pair of keys on the cap being configured to mate with a pair of keys on the gas specific adapter, the first and second spaced apart slots formed in the lip of the gas valve body and the first and second spaced apart tabs formed on the cap also being spaced apart at the predetermined angle.

3. The apparatus of claim 1, wherein the gas valve body is configured to be coupled to one of a gas block, a hose in an O/R column, and a hose barb and hose suspended from a ceiling as a pendant.

4. The apparatus of claim 1, wherein the gas valve body and the gas specific adapter are each configured to supply one of oxygen, air, nitrous oxide, nitrogen, carbon dioxide, helium and vacuum.

5. The apparatus of claim 1, wherein the first and second spaced apart slots and the first and second tabs are each spaced apart by an angle of 180°.

6. The apparatus of claim 1, wherein the first and second spaced apart slots and the first and second tabs are each spaced apart by an angle of 165°.

7. The apparatus of claim 1, wherein the first and second spaced apart slots and the first and second tabs are each spaced apart by an angle of 135°.

8. The apparatus of claim 1, wherein the first and second spaced apart slots and the first and second tabs are each spaced apart by an angle of 150°.

9. A gas valve apparatus configured to receive a gas specific adapter, the apparatus comprising:

a gas valve body having a first end configured to be coupled to a gas connection and a second end;

a keyed body configured to receive the second end of the gas valve body, the keyed body having a first keying mechanism; and a cap coupled to the keyed body, the cap including a keyed front face having a gas outlet configured to receive the gas specific adapter, the cap also including a second keying mechanism configured to mate with the first keying mechanism the keyed body to permit the cap to be coupled to the keyed body.

10. The apparatus of claim 9, wherein the first keying mechanism includes an annular groove having a predetermined diameter formed in the keyed body, and the second keying mechanism includes an annular flange formed on the cap, the annular flange having substantially the same predetermined diameter as the annular groove to permit the flange to mate with the groove formed in the keyed body.

11. The apparatus of claim 10, wherein the keyed body includes a cylindrical portion having inner and outer side walls, the annular groove being formed by a notch formed adjacent the inner side wall.

12. The apparatus of claim 11, wherein the annular flange of the cap includes an inner side wall and an outer side wall, the flange being formed to include a notched portion adjacent the outer side wall to permit the flange to be inserted into the annular groove.

13. The apparatus of claim 10, wherein the annular groove and the annular flange are each tapered surfaces.

14. The apparatus of claim 9, wherein the first keying mechanism includes an annular ring formed on the keyed body, the annular ring having a predetermined diameter, and the second keying mechanism includes an annular groove formed in the cap, the annular groove having substantially the same predetermined diameter as the annular ring to permit the annular ring to mate with the annular groove when the cap is installed on the keyed body.

15. The apparatus of claim 9, wherein the gas valve body includes a hex nut located between the first and second ends, and the keyed body is formed to include a hex portion configured to engage the hex nut on the valve body to prevent rotation of the keyed body relative to the gas valve body.

16. The apparatus of claim 9, wherein the gas valve body is secured to the keyed body by an adhesive.

17. The apparatus of claim 9, wherein the keyed body and the cap are made from a material having the same color.

18. The apparatus of claim 9, wherein the gas valve body is configured to be coupled to one of a gas block, a hose in an O/R column, and a hose barb and hose suspended from a ceiling as a pendant.

19. The apparatus of claim 9, wherein the gas valve body and the gas specific adapter are each configured to supply one of oxygen, air, nitrous oxide, nitrogen, carbon dioxide, helium and vacuum.

* * * * *